(12) United States Patent
Wigbers et al.

(10) Patent No.: US 8,536,377 B2
(45) Date of Patent: Sep. 17, 2013

(54) METHOD FOR PRODUCING N,N-SUBSTITUTED-3-AMINOPROPAN-1-OLS

(75) Inventors: Christof Wilhelm Wigbers, Mannheim (DE); Johann-Peter Melder, Böhl-Iggelheim (DE); Martin Ernst, Heidelberg (DE)

(73) Assignee: BASF SE (DE)

( * ) Notice: Subject to any disclaimer, the term of this patent is extended or adjusted under 35 U.S.C. 154(b) by 131 days.

(21) Appl. No.: 13/127,828

(22) PCT Filed: Nov. 2, 2009

(86) PCT No.: PCT/EP2009/064438
§ 371 (c)(1),
(2), (4) Date: Aug. 5, 2011

(87) PCT Pub. No.: WO2010/052181
PCT Pub. Date: May 14, 2010

(65) Prior Publication Data
US 2011/0288338 A1 Nov. 24, 2011

(30) Foreign Application Priority Data
Nov. 5, 2008 (EP) .................................... 08168371

(51) Int. Cl.
*C07C 213/00* (2006.01)
(52) U.S. Cl.
USPC ........................................................ 564/473
(58) Field of Classification Search
USPC ........................................................ 564/473
See application file for complete search history.

(56) References Cited

U.S. PATENT DOCUMENTS

| | | | |
|---|---|---|---|
| 2,558,520 | A | 6/1951 | Hoyt et al. |
| 4,954,982 | A | 9/1990 | Tateishi et al. |
| 5,079,266 | A | 1/1992 | Bockowski et al. |
| 5,426,249 | A | 6/1995 | Haas et al. |
| 5,463,130 | A | 10/1995 | Witzel et al. |
| 5,530,127 | A | 6/1996 | Reif et al. |
| 5,536,691 | A | 7/1996 | Breitscheidel et al. |
| 5,696,048 | A | 12/1997 | Breitscheidel et al. |
| 5,840,981 | A | 11/1998 | Fuchs et al. |
| 5,894,074 | A | 4/1999 | Fuchs et al. |
| 7,663,003 | B2 | 2/2010 | Huber-Dirr et al. |
| 7,915,454 | B2 | 3/2011 | Oftring et al. |
| 2001/0003136 | A1 | 6/2001 | Nouwen et al. |
| 2008/0064882 | A1 | 3/2008 | Huber-Dirr et al. |
| 2008/0071120 | A1 | 3/2008 | Houssin et al. |
| 2008/0146852 | A1 | 6/2008 | Dubois et al. |
| 2008/0299390 | A1 | 12/2008 | Houssin et al. |
| 2008/0319233 | A1 | 12/2008 | Dubois |
| 2009/0149314 | A1 | 6/2009 | Ernst et al. |
| 2009/0197981 | A1 | 8/2009 | Rekker et al. |
| 2011/0054167 | A1 | 3/2011 | Kubanek et al. |
| 2011/0218323 | A1 | 9/2011 | Dahmen et al. |

FOREIGN PATENT DOCUMENTS

| | | |
|---|---|---|
| CA | 2039328 A1 | 10/1991 |
| CA | 2105100 A1 | 3/1994 |
| CN | 1594109 A | 3/2005 |
| DE | 2445303 A1 | 4/1976 |
| DE | 4232424 A1 | 3/1994 |
| EP | 106600 A2 | 4/1984 |
| EP | 0449089 A1 | 10/1991 |
| EP | 598228 A1 | 5/1994 |
| EP | 0636409 A1 | 2/1995 |
| EP | 0673918 A1 | 9/1995 |
| EP | 0696572 A1 | 2/1996 |
| EP | 0742045 A1 | 11/1996 |
| EP | 0869113 A2 | 10/1998 |
| EP | 0963975 A1 | 12/1999 |
| EP | 1106600 A2 | 6/2001 |
| EP | 1852182 A1 | 11/2007 |
| GB | 653056 A | 5/1951 |
| GB | 1512797 A | 6/1978 |
| WO | WO-96/36589 A1 | 11/1996 |
| WO | WO-2004/085356 A1 | 10/2004 |
| WO | WO-2006/005505 A1 | 1/2006 |
| WO | WO-2006/005506 A1 | 1/2006 |
| WO | WO-2006/087083 A2 | 8/2006 |

(Continued)

OTHER PUBLICATIONS

Finch et al., Journal of the American Chemical Society (1952), 74, p. 2016-2018.*

(Continued)

*Primary Examiner* — Brian J Davis
(74) *Attorney, Agent, or Firm* — Novak Druce Connolly Bove + Quigg LLP

(57) ABSTRACT

The present invention relates to a process for preparing N,N-substituted 3-aminopropan-1-ols by
 a) reacting secondary amine with acrolein at a temperature of (−50) to 100° C. and a pressure of 0.01 to 300 bar, and
 b) reacting the reaction mixture obtained in stage a) with hydrogen and ammonia in the presence of a hydrogenation catalyst at a pressure of 1 to 400 bar,
wherein the molar ratio of secondary amine to acrolein in stage a) is 1:1 or more and the temperature in stage b) is in the range from (−50) to 70° C. In a preferred embodiment, acrolein which has been obtained from glycerol based on renewable raw materials is used. The invention further relates to the use of an N,N-dimethyl-3-aminopropan-1-ol (DMAPOL) based on renewable raw materials as a catalyst for polyurethane preparation, as a scrubbing fluid in gas scrubbing, in the electronics chemicals and electroplating sectors, as a feedstock in organic synthesis, and as an intermediate in the production of pharmaceuticals and crop protection compositions.

15 Claims, No Drawings

(56) References Cited

FOREIGN PATENT DOCUMENTS

| WO | WO-2007/090990 A2 | 8/2007 |
| WO | WO-2007/104663 A1 | 9/2007 |
| WO | WO-2010/052181 A2 | 5/2010 |
| WO | WO-2010/054988 A2 | 5/2010 |

OTHER PUBLICATIONS

International Preliminary Report on Patentability, PCT/EP2009/064438, May 19, 2011.

Perioid Table of the Elements, IUPAC version, Jun. 22, 2007, http://old.iupac.org/reports/periodic_table/IUPAC_Periodic_Table-22Jun07b.pdf.

International Preliminary Report on Patentability, PCT/EP2009/064438, English Translation issued May 6, 2011.

R. J. Bass et al., "The NMR Spectra of Basic Primary Alcohols", Tetrahedron Letters No. 24, pp. 1941-1942, (1969).

Yoshimi Hirokawa et al., "Synthesis and Structure-Activity Relationships of 4-Amino-5-chloro-$N$-(1,4-dialkylhexahydro-1,4-diazepin-6-yl)-2-methoxybenzamide Derivatives, Novel and Potent Serotonin 5-$HT_3$ and Dopamine $D_2$ Receptors Dual Antagonist", Chem. Pharm. Bull. vol. 50(7) pp. 941-959 (2002).

Antony Chesney et al., "Synthetic Approaches Towards Manzamine. An Easy Preparation of β-Amino Aldehydes", Synthetic Communications, vol., 20(20), pp. 3167-3180 (1990).

\* cited by examiner

METHOD FOR PRODUCING N,N-SUBSTITUTED-3-AMINOPROPAN-1-OLS

CROSS-REFERENCE TO RELATED APPLICATIONS

This application is a national stage application (under 35 U.S.C. §371) of PCT/EP2009/064438, filed Nov. 2, 2009, which claims benefit of European application 0816837.6, filed Nov. 5, 2008.

BACKGROUND OF THE INVENTION

The present invention relates to a process for preparing N,N-substituted 3-aminopropan-1-ols.

The preparation of N,N-substituted 3-aminopropan-1-ols is disclosed, for example, in European patent application EP-A1-0673918. N,N-substituted 3-aminopropan-1-ols are obtained by converting ethylene cyanohydrin and secondary amines over a palladium catalyst at elevated temperatures and pressures.

EP-A2-0869113 discloses the preparation of N,N-substituted 3-aminopropan-1-ols from ethylene cyanohydrin and secondary amines, such as dimethylamine, the reaction being performed at temperatures of 50 to 250° C., a pressure of 5 to 350 bar, in the presence of a palladium-comprising catalyst. The supported catalyst used comprises 0.1 to 10% by weight of palladium, based on the total weight of the catalyst, and at least one further metal selected from groups IB and VIII of the Periodic Table, cerium and lanthanum.

It was an object of the present invention to provide a process for preparing N,N-substituted 3-aminopropan-1-ols from acrolein. More particularly, it was an aim of the present invention to provide a new preparation route for industrially important N,N-substituted 3-aminopropan-1-ols, such as N,N-dimethyl-3-aminopropan-1-ol (DMAPOL), in which feedstocks which can be obtained on the basis of renewable raw materials are used. Acrolein can be prepared, for example, by dehydrating glycerol, which in turn can be obtained as a by-product from fat hydrolysis or biodiesel production. The use of renewable resources in the preparation of such products can contribute to preservation of petrochemical resources which are typically used. A further intention was to provide a process for preparing N,N-substituted 3-aminopropan-1-ols, in which N,N-substituted 3-aminopropan-1-ols are formed in high yield and high selectivity, and which is additionally technically easy to handle and has a high level of process economy.

The reaction of acrolein with secondary amines has already been described in DE-A-4232424 and by Finch et al. (H. D. Finch, E. A. Peterson and S. A. Ballard, J. Am. Chem. Soc., 74, 2016 (1952)).

In DE-A-4232424, from 2-alkenals and secondary amines, the corresponding N,N,N',N'-substituted unsaturated amines are obtained, which can be hydrogenated in a further reaction to the saturated amines. There is no indication that reaction of acrolein with secondary amines and subsequent hydrogenation can provide N,N-substituted 3-aminopropan-1-ols with high selectivity.

Finch et al. (H. D. Finch, E. A. Peterson and S. A. Ballard, J. Am. Chem. Soc., 74, 2016 (1952)) describe the reaction of acrolein or methacrolein with primary or secondary amines. The N,N'-substituted 1,3-propenediamines or N,N,N',N'-substituted 1,3-propenediamines thus obtained are, according to the disclosure, hydrogenated in a next stage to the corresponding saturated N,N'-substituted or N,N,N',N'-substituted 1,3-propanediamines or are heated together with other amines, such that an amine exchange takes place. It is stated that amine exchange and hydrogenation can also be performed simultaneously in the presence of a Raney® nickel catalyst. Thus, a mixture of isopropylpropylamine and N-isopropyl-1,3-propanediamine was obtained in two stages, by, in the first stage, first reacting acrolein and isopropylamine, and, in a second stage, hydrogenating the resulting reaction mixture, after removal of excess amine and solvent, with ammonia in the presence of Raney® nickel at a temperature of 105° C. There is no indication that N,N-substituted 3-aminopropan-1-ols can be formed with high selectivity.

BRIEF SUMMARY OF THE INVENTION

It has now been found that, surprisingly, by virtue of a specific selection and combination of process parameters, N,N-substituted 3-aminopropan-1-ols can be formed with high selectivity from acrolein and secondary amines.

According to the invention, the object is achieved by a process for preparing N,N-substituted 3-aminopropan-1-ols by a) reacting secondary amine with acrolein at a temperature of (−50) to 100° C. and a pressure of 0.01 to 300 bar, and b) reacting the reaction mixture obtained in stage a) with hydrogen and ammonia in the presence of a hydrogenation catalyst at a pressure of 1 to 400 bar, wherein the molar ratio of secondary amine to acrolein in stage a) is 1:1 or more and the temperature in stage b) is in the range from (−50) to 70° C.

DETAILED DESCRIPTION OF THE INVENTION

In the first stage a) of the process according to the invention, acrolein is reacted with secondary amine.

The acrolein used in the reaction is typically obtained by oxidizing propene or by dehydrating glycerol.

Typically, acrolein is prepared by oxidizing propene. An overview of acrolein preparation by propene oxidation can be found, for example, in the Ullmann (Ullmann's Encyclopedia of Industrial Chemistry, Acrolein and Methacrolein, Chapter 3.1 "Acrolein by Propene Oxidation", Wiley-VCH-Verlag, Electronic Edition, 2007).

In a preferred embodiment, however, acrolein which has been obtained by dehydrating glycerol is used. The preparation of acrolein by dehydrating glycerol is disclosed, for example, in WO-A2-2006087083, EP-B1-598228, WO-A1-2007090990, U.S. Pat. No. 5,079,266, U.S. Pat. No. 2,558,520 or by Chai et al. (S. H. Chai, H. P. Wang, Y. Lang, B. Q. Xu, Journal of Catalysis, 250 (2), 342-349 (2007)).

Glycerol is obtained typically as a by-product in the conversion of fats and oils to fatty acids (fat hydrolysis) or fatty acid methyl esters (biodiesel). The preparation of glycerol from fats and oils is described, for example, in the Ullmann (Ullmann's Encyclopedia of Industrial Chemistry, Glycerol, Chapter 4.1 "Glycerol from Fat and Oils", Wiley-VCH-Verlag, Electronic Edition, 2007).

Glycerol can also be prepared proceeding from the petrochemical starting material of propene. An overview of the synthesis of glycerol from propene is likewise given in the Ullmann (Ullmann's Encyclopedia of Industrial Chemistry, "Glycerol", Chapter 4.1 "Synthesis from Propene", Wiley-VCH-Verlag, Electronic Edition, 2007).

For the process according to the invention, the preparation route by which glycerol has been obtained is generally unimportant. Glycerol on a vegetable, animal or petrochemical basis is suitable as a starting material for the process according to the invention.

In a very particularly preferred embodiment, glycerol based on renewable raw materials is used as the starting material in the preparation of acrolein, for example glycerol obtained as a by-product from fat hydrolysis or biodiesel production. This particular embodiment has the advantage that industrially significant aminoalcohols, such as DMAPOL, can be obtained from renewable resources. The use of renewable resources in the preparation of such products can contribute to preservation of the petrochemical resources which are typically used.

Preference is given to using, in the process according to the invention, acrolein with an acrolein content of at least 95%, preferably at least 98% and more preferably at least 99%.

A further feedstock used in the process according to the invention is secondary amine.

The secondary amines used may be aliphatic, cycloaliphatic or cyclic secondary amines.

The cyclic secondary amine used may, for example, be pyrrolidine, imidazole, piperidine, morpholine or piperazine.

Preference is given to using secondary amines of the formula (I)

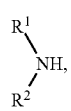

(I)

where the $R^1$ and $R^2$ radicals are each defined as follows:
$R^1$ and $R^2$ are identically or each independently a straight-chain or branched or a cyclic hydrocarbon radical having 1 or 3 to 20 carbon atoms, where the hydrocarbon radical may be mono- or polyunsaturated.

For example, $R^1$ and/or $R^2$ may be defined as follows:
$C_1$-$C_6$-alkyl: e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;
$C_1$-$C_{12}$-alkyl: e.g. $C_1$-$C_6$-alkyl as specified above, and also heptyl, 2-methylhexyl, 3-methylhexyl, 2,2-dimethylpentyl, 2,3-dimethylpentyl, 2,4-dimethylpentyl, 3,3-dimethylpentyl, 2,2-dimethyl-3-methylbutyl, octyl, 2-methylheptyl, 3-methylheptyl, 4-methylheptyl, 2,2-dimethylhexyl, 2,3-dimethylhexyl, 2,4-dimethylhexyl, 3,3-dimethylhexyl, 2,2-dimethyl-3-methylpentyl, 2-methyl-3,3-dimethylpentyl, 2,3,4-trimethylpentyl and 2,2,3,3-tetramethylbutyl, 1-nonyl, 1-decyl, 1-undecyl or 1-dodecyl;
$C_1$-$C_{20}$-alkyl; e.g. $C_1$-$C_{12}$-alkyl as specified above, and also 1-tridecyl, 1-tetradecyl, 1-pentadecyl, 1-hexadecyl, 1-heptadecyl, 1-octadecyl, nonadecyl or eicosyl;
$C_3$- to $C_8$-cycloalkyl: e.g. cyclopropyl, cyclobutyl, cyclopentyl, cyclohexyl or cyclooctyl;
$C_3$- to $C_{12}$-cycloalkyl: $C_3$- to $C_8$-cycloalkyl as specified above, and also cyclododecyl;
$C_2$-$C_6$-alkenyl: e.g. ethenyl, propenyl, butenyl, pentenyl or hexenyl;
$C_2$-$C_{20}$-alkenyl: e.g. $C_2$-$C_6$-alkenyl as specified above, and also heptenyl, octenyl, nonenyl or decenyl;
$C_3$-$C_6$-cycloalkenyl: e.g. cyclopropenyl, cyclobutenyl, cyclopentenyl, or cyclohexenyl;

aryl: mono- to tricyclic aromatic carbocycle having 6 to 14 ring members, for example phenyl, naphthyl or anthracenyl;
heteroaryl: e.g. thienyl, furyl, pyrazolyl, imidazolyl, thiazolyl and oxazolyl; or
$C_7$-$C_{12}$-aralkyl, for example phenylmethyl, 1-phenylethyl, 2-phenylethyl, 1-phenylpropyl, 2-phenylpropyl or 3-phenylpropyl.

The $R^1$ and $R^2$ radicals may optionally be substituted, the substituents being variable within a wide range.

$R^1$ and $R^2$ are preferably identically or each independently a straight-chain or branched hydrocarbon radical having 1 or 3 to 20 carbon atoms, the hydrocarbon radical being saturated.

When secondary amines of the formula (I) whose substituents $R^1$ and/or $R^2$ comprise unsaturated bonds are used, hydrogenation of these substituents may also occur.

Preference is given to using dimethylamine, diethylamine, di-n-propylamine, diisopropylamine, isopropylethylamine, di-n-butylamine, di-s-butylamine or dicyclohexylamine as secondary amines in the process.

Particular preference is given to using dimethylamine or diethylamine, especially preferably dimethylamine, in the reaction.

According to the invention, the molar ratio of acrolein to secondary amine is 1:1 or more. In general, the molar ratio of secondary amine to acrolein is in the range from 1.4:1 to 200:1, preferably 1.8:1 to 100:1, more preferably 2:1 to 50:1, especially preferably 2:1 to 10:1 and most preferably 2:1 to 5:1.

The reaction of acrolein with secondary amine can be effected without catalyst or in the presence of a catalyst.

Useful catalysts include, for example, solid Brønsted or Lewis acids, as described, for example, in EP-A1-449089 (page 2 column 2 lines 11-20) and in the article by Tanabe et al. (K. Tanabe, Studies in Surface Science and Catalysis, Vol. 51, 1989, p. 1 ff). Examples here include acidic metal oxide catalysts, such as aluminum oxide, titanium dioxide, zirconium dioxide and silicon dioxide. Inorganic or organic ion exchangers laden with ammonium ions are also useful, such as zeolites or sulfonated copolymers of styrene and divinylbenzene (e.g. of the Lewatit® brand from Lanxess, Amberlite® brand from Rohm & Haas) or ion exchangers based on siloxane (for example of the Deloxan® brand from Degussa).

Acrolein can be reacted with secondary amine in the presence of a solvent, for example in ethers such as methyl tert-butyl ether, ethyl tert-butyl ether or tetrahydrofuran (THF); alcohols such as methanol, ethanol or isopropanol; hydrocarbons such as hexane, heptane or raffinate cuts; aromatics such as toluene; amides such as dimethylformamide or dimethylacetamide, or lactams such as N-methylpyrrolidone, N-ethylpyrrolidone, N-methylcaprolactam or N-ethylcaprolactam. Useful solvents also include suitable mixtures of the solvents listed above. A preferred solvent is THF. The solvent can be used in a proportion of 5 to 95% by weight, preferably 20 to 70%, more preferably 30 to 60%, based in each case on the total weight of the reaction mixture, the total weight of the reaction mixture being composed of the sum of the masses of the starting materials and solvents used in the process. Preference is given to performing the reaction of acrolein with secondary amine without an addition of solvent.

Acrolein is reacted with secondary amine at temperatures of (−50) to 100° C., preferably (−20) to 70° C., more preferably (−10) to 40° C., and pressures of 0.01 to 300 bar, preferably 0.1 to 200 bar, more preferably 1 to 200 bar, most preferably standard pressure (atmospheric pressure). In the case of gaseous secondary amines, such as dimethylamine, the reaction is performed preferably at pressures of 5 to 400 bar, more preferably 10 to 300 bar, especially 15 to 200 bar.

The reaction of acrolein with secondary amine can be carried out either batchwise or continuously.

The batchwise reaction of acrolein with secondary amine can be effected, for example, in a stirred autoclave, a bubble column or a circulation reactor, for instance a jet loop reactor.

In the batchwise reaction of acrolein with secondary amine, typically secondary amine or a suspension of secondary amine and catalyst and optionally solvent is initially charged in the reactor. In order to ensure a high conversion and high selectivity, the suspension of secondary amine and catalyst is typically mixed thoroughly with acrolein, for example by means of a turbine stirrer in an autoclave.

The suspended catalyst material can be introduced and removed again with the aid of customary techniques (sedimentation, centrifugation, cake filtration, crossflow filtration). The catalyst can be used once or more than once.

When the reaction of acrolein with secondary amine is effected in the presence of a catalyst, the catalyst concentration is advantageously 0.1 to 50% by weight, preferably 0.5 to 40% by weight, more preferably 1 to 30% by weight, especially 5 to 20% by weight, based in each case on the total weight of the suspension consisting of secondary amine and catalyst.

The mean catalyst particle size is advantageously in the range from 0.001 to 1 mm, preferably in the range from 0.005 to 0.5 mm, especially 0.01 to 0.25 mm.

The reaction of acrolein with secondary amine is preferably performed continuously, typically in pressure vessels or pressure vessel cascades.

Preference is given to passing acrolein and secondary amine through a tubular reactor, in which the catalyst is arranged in the form of a fixed bed.

In general, acrolein and the secondary amine are mixed thoroughly before being introduced into the pressure vessel or within the pressure vessel. The mixing can be effected, for example, before the introduction using static mixers.

In the pressure vessel, internals or mixing elements may also be introduced, which improve the mixing of acrolein and secondary amine. Mixing can optionally also be effected by means of installed stirrers or by pumped circulation of the reaction mixture.

In the continuous reaction of acrolein with secondary amine, preference is given to establishing a catalyst hourly space velocity of 0.01 to 10 kg, preferably 0.05 to 7 kg and more preferably 0.1 to 5 kg of acrolein per kg of catalyst and hour.

The reaction mixture obtained in stage a) typically comprises N,N,N',N'-substituted 1,3-propenediamine.

The reaction mixture obtained in stage a) can be worked up before use in stage b), in order to concentrate the N,N,N',N'-substituted 1,3-propenediamine, for example by distillation or rectification.

However, the reaction mixture obtained in stage a) is preferably, before use in stage b), used without additional purification or workup.

In stage b), the reaction mixture obtained in stage a) is reacted with hydrogen and ammonia in the presence of a hydrogenation catalyst.

Hydrogen is used in the process according to the invention.

The hydrogen is used generally in technically pure form. The hydrogen can also be used in the form of a hydrogen-comprising gas, i.e. in admixtures with other inert gases, such as nitrogen, helium, neon, argon or carbon dioxide. The hydrogen-comprising gases used may, for example, be reformer offgases, refinery gases, etc., when and provided that these gases do not comprise any catalyst poisons for the hydrogenation catalysts used, for example CO. However, preference is given to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

Ammonia is also used in the process according to the invention.

The ammonia used may be conventionally commercially available ammonia, for example ammonia having a content of more than 98% by weight of ammonia, preferably more than 99% by weight of ammonia, preferably more than 99.5% by weight, especially more than 99.9% by weight of ammonia.

The molar ratio of the ammonia used in stage b) to the acrolein used in stage a) is preferably 1:1 to 1000:1, preferably 2:1 to 100:1, more preferably 4:1 to 50:1.

The reaction can also be performed in the presence of water.

The amount of water is preferably selected such that the molar ratio of water to acrolein which was used in stage a) is in the range from 0.01:1 to 2:1, preferably in the range from 0.1:1 to 1.8:1, more preferably 0.3:1 to 1.7:1, especially preferably 0.4:1 to 1.6:1. The water and the reaction mixture obtained in stage a) can be added together to stage b), for example as a premixed reactant stream, or separately. In the case of separate addition, water and the reaction mixture obtained in stage a) can be added to stage b) simultaneously, with a time interval or successively. It is also possible that the addition of water is performed as early as before the performance of stage a) and is already present in stage a), since the presence of water does not significantly affect stage a). However, preference is given to not adding the water until before the start of stage b).

The process according to the invention is performed in the presence of a hydrogenation catalyst.

The hydrogenation catalysts used in the process according to the invention comprise one or more metals of groups 8 and/or 9 and/or 10 and/or 11 of the Periodic Table of the Elements (Periodic Table in the IUPAC version of 06.22.2007, http://www.iupac.org/reports/periodic_table/IUPAC_Periodic_Table-22Jun07b.pdf). Examples of such metals are Cu, Co, Ni and/or Fe, and also noble metals such as Rh, Ir, Ru, Pt, Pd, and Re.

The hydrogenation catalyst can be used in the process in metallic form, for example in the form of metal meshes or grids, or in the form of Raney sponge or skeletal catalysts. In a preferred embodiment, the metals are used in the process according to the invention in the form of Raney sponge or skeletal catalysts. Particular preference is given to using Raney nickel and/or cobalt catalysts.

Raney nickel or cobalt catalysts are prepared typically by treating an aluminum-nickel or an aluminum-cobalt alloy with concentrated sodium hydroxide solution, which leaches out the aluminum and forms a metallic nickel or cobalt sponge. The preparation of Raney catalysts is described, for example, in the Handbook of Heterogeneous Catalysis (M. S. Wainright in G. Ertl, H. Knözinger, J. Weitkamp (eds.), Handbook of Heterogeneous Catalysis, Vol. 1, Wiley-VCH, Weinheim, Germany 1997, page 64 ff.). Such catalysts are available, for example, as Raney® catalysts from Grace, or as Sponge Metal® catalysts from Johnson Matthey.

In a preferred embodiment, Raney cobalt catalysts are used in the process according to the invention.

The molar proportion of cobalt atoms based on the sum of all metal atoms in the hydrogenation catalyst used, which was used in the process in metallic form, is preferably 50 mol % and more, more preferably 75 mol %, even more preferably 90 mol % and more, especially preferably 99 mol % and more.

The composition of the hydrogenation catalyst which is used in metallic form can be measured by means of atomic absorption spectrometry (AAS), atomic emission spectrometry (AES), X-ray fluorescence analysis (RFA) or ICP-OES (Inductively Coupled Plasma Optical Emission Spectrometry).

The hydrogenation catalysts usable in the process according to the invention can also be prepared by reducing so-called catalyst precursors.

The catalyst precursor comprises an active material which comprises one or more catalytically active components and optionally a carrier material.

The catalytically active components are oxygen compounds of the metals of groups 8 and/or 9 and/or 10 and/or 11 of the Periodic Table of the Elements (Periodic Table in the IUPAC version of 06.22.2007). Examples of such metals are Cu, Co, Ni and/or Fe, and also noble metals such as Rh, Ir, Ru, Pt, Pd and Re, which are present as oxygen compounds—for example metal oxides or hydroxides, such as CoO, NiO, CuO or $RuO(OH)_x$.

Preferred metals are Cu, Co, Ni and/or Fe, and also noble metals such as Rh, Ir, Ru, Pt and Pd. Very particularly preferred metals are Cu, Ni and/or Co.

In a particularly preferred embodiment, the catalyst precursor of the hydrogenation catalyst comprises oxygen compounds of cobalt as the catalytically active component, for example in the form of CoO and/or in the form of a mixed oxide of cobalt, such as $LiCoO_2$. The catalyst precursor of the hydrogenation catalyst preferably comprises CoO as the catalytically active component. In this preferred embodiment, the catalyst precursor of the hydrogenation catalyst may comprise further catalytically active components as well as oxygen compounds of cobalt. The molar proportion of cobalt atoms based on the sum of all metal atoms present in the catalytically active components used is, in this preferred embodiment, preferably 10 mol % or more, more preferably 30 mol % or more, even more preferably 50 mol % or more, especially 90 mol % or more. The atomic composition of the catalytically active components can be measured by means of atomic absorption spectrometry (AAS), atomic emission spectrometry (AES), X-ray fluorescence analysis (RFA) or ICP-OES (Inductively Coupled Plasma Optical Emission Spectrometry).

In the context of this application, the term "catalytically active components" is used for the abovementioned oxygen-metal compounds, but is not intended to imply that these oxygen compounds themselves are already catalytically active. The catalytically active components generally only have catalytic activity in the inventive reaction on completion of reduction.

In the context of this invention, the mass of the active material is defined as the sum of the mass of the support material and of the mass of the catalytically active components.

The catalyst precursors used in the process may comprise, as well as the active material, shaping agents such as graphite, stearic acid, phosphoric acid or further processing assistants.

The catalyst precursors used in the process may further comprise one or more doping elements (oxidation state 0) or the inorganic or organic compounds thereof, selected from groups 1 to 14 of the Period Table. Examples of such elements or compounds thereof are: transition metals such as Mn or manganese oxides, Re or rhenium oxides, Cr or chromium oxides, Mo or molybdenum oxides, W or tungsten oxides, Ta or tantalum oxides, Nb or niobium oxides or niobium oxalate, V or vanadium oxides or vanadyl pyrophosphate, zinc or zinc oxides, silver or silver oxides, lanthanides such as Ce or $CeO_2$ or Pr or $Pr_2O_3$, alkali metal oxides such as $K_2O$, alkali metal carbonates such as $Na_2CO_3$ and $K_2CO_3$, alkaline earth metal oxides such as SrO, alkaline earth metal carbonates such as $MgCO_3$, $CaCO_3$, $BaCO_3$, tin or tin oxides, phosphoric anhydrides and boron oxide ($B_2O_3$).

In the process according to the invention, the catalyst precursors are preferably used in the form of catalyst precursors which consist only of catalytically active material, optionally a shaping assistant (for example graphite or stearic acid) if the catalyst is used as a shaped body, and optionally one or more doping elements, but apart from that do not comprise any further catalytically active accompanying substances. In this context, the support material is considered to form part of the catalytically active material.

The compositions specified hereinafter relate to the composition of the catalyst precursor after the last heat treatment thereof, which is generally a calcination, and before the reduction thereof with hydrogen. The proportion of the active material based on the total mass of the catalyst precursor is typically 50% by weight or more, preferably 70% by weight or more, more preferably 80 to 100% by weight, even more preferably 90 to 99% by weight, especially 92 to 98% by weight.

The catalyst precursors can be prepared by known processes, for example by precipitation reactions (for example coprecipitation or precipitative application) or impregnation.

In a preferred embodiment, catalyst precursors which are prepared by impregnation of support materials (impregnated catalyst precursors) are used in the process according to the invention.

The support materials which are used in the impregnation can be used, for example, in the form of powders or shaped bodies, such as extrudates, tablets, spheres or rings. Support material suitable for fluidized bed reactors is preferably obtained by spray drying.

Useful support materials include, for example, carbon, such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary processes (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the catalytically active components or of the doping elements. The impregnation can also be effected with other suitable soluble compounds of the elements in question.

Thereafter, the impregnated support material is generally dried and calcined. The drying is effected typically at temperatures of 80 to 200° C., preferably 100 to 150° C. The calcination is performed generally at temperatures of 300 to 800° C., preferably 400 to 600° C., more preferably 450 to 550° C.

The impregnation can also be effected by the so-called "incipient wetness method", in which the support material, according to its water absorption capacity, is moistened with the impregnation solution up to saturation at most. However, the saturation can also be effected in supernatant solution.

In the case of multistage impregnation processes, it is appropriate to dry and optionally to calcine between individual impregnation steps. Multistage impregnation should advantageously be employed when the support material is to be contacted with metal salts in a relatively large amount.

To apply a plurality of components to the support material, the impregnation can, for example, be effected simultaneously with all metal salts or in any sequence of the individual metal salts in succession.

The catalyst precursors obtained by impregnation comprise the catalytically active components in the form of a mixture of their oxygen compounds, i.e. especially as the oxides, mixed oxides and/or hydroxides. The catalyst precursors thus prepared can be stored as such.

In a further preferred embodiment, catalyst precursors are prepared by means of a coprecipitation of all of their components. To this end, a soluble salt of the catalytically active components or of the doping elements and optionally a soluble compound of a support material in a liquid are generally admixed with a precipitant under hot conditions and with stirring until precipitation is complete.

The liquid used is generally water.

Useful soluble salts of the corresponding catalytically active components include typically the corresponding nitrates, sulfates, acetates or chlorides, of the metals of groups 8 and/or 9 and/or 10 and/or 11 of the Periodic Table of the Elements (Periodic Table in the IUPAC version of 06.22.2007). Examples of such metals are Cu, Co, Ni and/or Fe, and also noble metals such as Rh, Ir, Ru, Pt and Pd. In addition, useful soluble salts also include corresponding compounds of the doping elements.

The water-soluble compounds of a support material used are generally water-soluble compounds of Al, Zr, Si, etc., for example the water-soluble nitrates, sulfates, acetates or chlorides of these elements.

Catalyst precursors can also be prepared by precipitative application. Precipitative application is understood to mean a preparation method in which a sparingly soluble or insoluble support material is suspended in a liquid and then soluble metal salts of the corresponding metal oxides are added, which are then precipitated onto the suspended support by adding a precipitant (for example described in EP-A2-1 106 600, page 4, and A. B. Stiles, Catalyst Manufacture, Marcel Dekker, Inc., 1983, page 15).

Examples of sparingly soluble and insoluble support materials include carbon compounds, such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water. Useful soluble metal salts of the corresponding catalytically active components generally include the corresponding nitrates, sulfates, acetates or chlorides of the metals of groups 8 and/or 9 and/or 10 and/or 11 of the Periodic Table of the Elements (Periodic Table in the IUPAC version of 06.22.2007). Examples of such metals are Cu, Co, Ni and/or Fe and/or Sn, and also noble metals such as Rh, Ir, Ru, Pt and Pd. In addition, useful soluble salts also include corresponding compounds of the doping elements.

In the precipitation reactions (coprecipitation or precipitative application), the type of soluble metal salts used is generally not critical. Since the principal factor in this procedure is the water solubility of the salts, one criterion is their good water solubility, which is essential for the preparation of these comparatively highly concentrated salt solutions. It is considered to be obvious that, in the selection of the salts of the individual components, of course only salts with those anions which do not lead to disruption, whether by causing undesired precipitation reactions or by complicating or preventing precipitation by complexation, are selected.

Typically, in the precipitation reactions, the soluble compounds are precipitated as sparingly soluble or insoluble, basic salts by adding a precipitant.

The precipitants used are preferably aqueous alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be carried out, for example, at temperatures of 20 to 100° C., particularly 30 to 90° C., especially 50 to 70° C.

The precipitates obtained in the precipitation reactions are generally chemically inhomogeneous and comprise generally mixtures of the oxides, oxide hydrates, hydroxides, carbonates and/or hydrogencarbonates of the metals used. It may be found to be favorable for the filterability of the precipitates when they are aged, i.e. when they are left for a certain time after the precipitation, optionally under hot conditions or while passing air through.

The precipitates obtained by these precipitation processes are typically processed by washing, drying, calcining and conditioning them.

After washing, the precipitates are dried generally at 80 to 200° C., preferably 100 to 150° C., and then calcined.

The calcination is performed generally at temperatures between 300 and 800° C., preferably 400 to 600° C., especially at 450 to 550° C.

After the calcination, the catalyst precursors obtained by precipitation reactions are typically conditioned.

The conditioning can be effected, for example, by adjusting the precipitated catalyst to a particular particle size by grinding.

After the grinding, the catalyst precursor obtained by precipitation reactions can be mixed with shaping assistants, such as graphite or stearic acid, and processed further to shaped bodies.

Common processes for shaping are described, for example, in the Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff.].

As described in the references cited, the process for shaping can be used to obtain shaped bodies in any three-dimensional shape, for example round, angular, elongated or the like, for example in the form of extrudates, tablets, granule, spheres, cylinders or pellets. Common processes for shaping are, for example, extrusion, tableting, i.e. mechanical pressing or pelletization, i.e. compaction by circular and/or rotating motions.

The conditioning or shaping is generally followed by a heat treatment. The temperatures in the heat treatment correspond typically to the temperatures in the calcination.

The catalyst precursors obtained by precipitation reactions comprise the catalytically active components in the form of a mixture of their oxygen compounds, i.e. especially as oxides, mixed oxides and/or hydroxides. The catalyst precursors thus prepared can be stored as such.

In a particularly preferred embodiment of the process according to the invention, the active material of the catalyst precursor does not comprise any support material. Catalysts which do not comprise any support material in the active material are generally obtained by coprecipitation.

The active material of catalyst precursors which do not comprise any support material preferably comprises one or more active components selected from the group consisting of CoO, NiO, CuO, RuO(OH)$_x$ and LiCoO$_2$.

The active material of catalyst precursors which do not comprise any support material more preferably comprises NiO and/or CoO, especially CoO.

Such catalyst precursors are, for example, catalysts which are disclosed in patent application PCT/EP2007/052013 and comprise, before the reduction with hydrogen, a) cobalt and b) one or more elements of the alkali metal group, of the alkaline earth metal group, of the group of the rare earths or zinc or mixtures thereof, where the elements a) and b) are present at least partly in the form of their mixed oxides, for example LiCoO$_2$, or particularly preferred catalysts which are disclosed in EP-A-0636409 and whose catalytically active material, before the reduction with hydrogen, comprises 55 to 98% by weight of Co, calculated as CoO, 0.2 to 15% by weight of phosphorus, calculated as H$_3$PO$_4$, 0.2 to 15% by weight of manganese, calculated as MnO$_2$, and 0.2 to 15% by weight of alkali metal, calculated as M$_2$O (M=alkali metal), or catalysts which are disclosed in EP-A-0742045 and whose catalytically active material, before the reduction with hydrogen, comprises 55 to 98% by weight of Co, calculated as CoO, 0.2 to 15% by weight of phosphorus, calculated as H$_3$PO$_4$, 0.2 to 15% by weight of manganese, calculated as MnO$_2$, and 0.05 to 5% by weight of alkali metal, calculated as M$_2$O (M=alkali metal).

Catalyst precursors which comprise mixed oxides of cobalt, such as LiCoO$_2$, and which preferably do not comprise any support material, can generally be prepared by thermal treatment of the corresponding compounds of cobalt and one or more compounds of the alkali metal group, of compounds of the alkaline earth metal group, of compounds from the group of the rare earths or of compounds of zinc, for example the nitrates, carbonates, hydroxides, oxides, acetates, oxalates or citrates. Thermal treatment can be understood, for example, as the co-melting or calcination of the abovementioned compounds. The thermal treatment of the abovementioned compounds, such as the nitrates, carbonates, hydroxides, oxides, can be effected under air. In a preferred embodiment, the thermal treatment, especially of the carbonates, is effected under an inert gas atmosphere. Examples of suitable inert gases include nitrogen, carbon dioxide, helium, neon, argon, xenon, krypton or mixtures of the inert gases mentioned. Nitrogen is preferentially suitable.

Processes for preparing LiCoO$_2$ are described, for example, in Antolini [E. Antolini, Solid State Ionics, 159-171 (2004)] and Fenton et al. [W. M. Fenton, P. A. Huppert, Sheet Metal Industries, 25 (1948), 2255-2259).

The catalyst precursor used, which preferably does not comprise any support material, may also be LiCoO$_2$, which is obtained by recycling batteries. A method of recycling or recovering lithium cobaltite from used batteries can be derived, for example, from CN-A-1594109. Mechanical opening of the battery and the leaching out of aluminum constituents with conc. NaOH can provide an LiCoO$_2$-rich filtercake.

In a further preferred embodiment, the active material comprises—in addition to the catalytically active components—support material.

Catalysts which comprise support material in the active material are generally obtained by precipitative application or impregnation.

Catalyst precursors which comprise support material may comprise one or more catalytically active components, preferably CoO, NiO, CuO and/or oxygen compounds of Rh, Ru, Pt, Pd and/or Ir.

The active material of catalyst precursors which comprise support material more preferably comprises CuO, NiO and/or CoO, especially CoO.

The support materials used are preferably carbon, such as graphite, carbon black and/or activated carbon, aluminum oxide (gamma, delta, theta, alpha, kappa, chi or mixtures thereof), silicon dioxide, zirconium dioxide, zeolites, aluminosilicates, etc., and mixtures of these support materials.

The proportion of support material in the active material can vary over a wide range according to the preparation method selected.

In the case of catalyst precursors which are prepared by impregnation, the proportion of support material in the active material is generally more than 50% by weight, preferably more than 75% by weight and more preferably more than 85% by weight. In the case of catalyst precursors which are prepared by precipitation reactions, such as coprecipitation or precipitative application, the proportion of support material in the active material is generally in the range from 10 to 90% by weight, preferably in the range from 15 to 80% by weight and more preferably in the range from 20 to 70% by weight.

Such catalyst precursors which are obtained by precipitation reactions are, for example, catalysts which are disclosed in EP-A-696572 and whose catalytically active material, before the reduction with hydrogen, comprises 20 to 85% by weight of ZrO$_2$, 1 to 30% by weight of oxygen compounds of copper, calculated as CuO, 30 to 70% by weight of oxygen compounds of nickel, calculated as NiO, 0.1 to 5% by weight of oxygen compounds of molybdenum, calculated as MoO$_3$, and 0 to 10% by weight of oxygen compounds of aluminum and/or manganese, calculated as Al$_2$O$_3$ and MnO$_2$ respectively, for example the catalyst which is disclosed in loc. cit, page 8, and has the composition of 31.5% by weight of ZrO$_2$, 50% by weight of NiO, 17% by weight of CuO and 1.5% by weight of MoO$_3$, or catalysts which are disclosed in EP-A-963 975 and whose catalytically active material, before the reduction with hydrogen, comprises 22 to 40% by weight of ZrO$_2$, 1 to 30% by weight of oxygen compounds of copper, calculated as CuO, 15 to 50% by weight of oxygen compounds of nickel, calculated as NiO, where the molar Ni:Cu ratio is greater than 1, 15 to 50% by weight of oxygen compounds of cobalt, calculated as CoO, 0 to 10% by weight of oxygen compounds of aluminum and/or of manganese, calculated as Al$_2$O$_3$ and MnO$_2$ respectively, and no oxygen compounds of molybdenum, for example the catalyst A which is disclosed in loc. cit., page 17, and has the composition of 33% by weight of Zr, calculated as ZrO$_2$, 28% by weight of Ni, calculated as NiO, 11% by weight of Cu, calculated as CuO, and 28% by weight of Co, calculated as CoO, or copper catalysts disclosed in DE-A-2445303, for example the precipitated copper catalyst disclosed in example 1 there, which is prepared by treating a solution of copper nitrate and aluminum nitrate with sodium bicarbonate and then washing, drying and heat treating the precipitate, and has a composition of approx. 53% by weight of CuO and approx. 47% by weight of Al$_2$O$_3$, or catalysts disclosed in WO 96/36589, especially those which comprise Ir, Ru and/or Rh, and activated carbon as the support material, or catalysts which are disclosed in EP-A2-1106600 and whose catalytically active material, before the reduction with hydrogen, comprises 22 to 45% by weight of oxygen compounds of zirconium, calculated as $ZrO_2$, 1 to 30% by weight of oxygen compounds of copper, calculated as CuO, 5 to 50% by weight of oxygen compounds of nickel, calculated as NiO, where the molar ratio of nickel to copper is greater than 1, 5 to 50% by weight of oxygen compounds of cobalt, calculated as CoO, 0 to 5% by weight of oxygen compounds of molybdenum, calculated as $MoO_3$, and 0 to 10% by weight of oxygen compounds of aluminum and/or of manganese, calculated as $Al_2O_3$ and $MnO_2$ respectively; or catalysts which are disclosed in EP-A-1852182 and comprise cobalt on a ZnO support and have the following particle size distribution: <10% of the particles have a particle size below one μm, 70-99% of the particles have a particle size between 1 and 5 μm and <20% of the particles have a particle size of more than 5 μm, or catalysts which are disclosed in WO 2004085356, WO 2006005505 and WO 2006005506 and whose catalytically active material comprises an oxidic material which comprises copper oxide (with a proportion in the range of $50 \leqq x \leqq 80$, preferably $55 \leqq x \leqq 75\%$ by weight), aluminum oxide (with a proportion in the range of $15 \leqq y \leqq 35$, preferably $20 \leqq y \leqq 30\%$ by weight) and lanthanum oxide (with a proportion in the range of $1 \leqq z \leqq 0$, preferably 2 to 25% by weight), based in each case on the total weight of the oxidic material after calcination, where: $80 \leqq x+y+z \leqq 100$, especially $95 \leqq x+y+z \leqq 100$, and also metallic copper powder, copper flakes or cement powder or a mixture thereof with a proportion in the range from 1 to 40% by weight, based on the total weight of the oxidic material, and graphite with a proportion of 0.5 to 5% by weight, based on the total weight of the oxidic material, where the sum of the proportions of oxidic material, metallic copper powder, copper flakes or cement powder or a mixture thereof and graphite adds up to at least 95% by weight of the shaped body produced from this material.

In a preferred embodiment, before they are used as catalysts in the process according to the invention, the catalyst precursors which have been obtained as described above by impregnation or precipitation are generally prereduced by treatment with hydrogen after the calcination or conditioning.

For the prereduction, the catalyst precursors are generally first exposed to a nitrogen-hydrogen atmosphere at 150 to 200° C. over a period of 12 to 20 hours and then treated in a hydrogen atmosphere at 200 to 400° C. for another up to approx. 24 hours. This prereduction reduces some of the oxygen-metal compounds present in the catalyst precursors to the corresponding metals, such that they are present together with the different kinds of oxygen compounds in the active form of the catalyst.

In a particularly preferred embodiment, the prereduction of the catalyst precursor is undertaken in the same reactor in which the process according to the invention is subsequently performed.

The catalyst thus formed can, after the prereduction, be handled and stored under an inert gas such as nitrogen, or under an inert liquid, for example an alcohol, water or the product of the particular reaction for which the catalyst is used. However, after the prereduction, the catalyst can also be passivated, i.e. provided with a protective oxide layer, with an oxygen-comprising gas stream such as air or a mixture of air with nitrogen.

The storage of the catalysts which have been obtained by prereduction of catalyst precursors under inert substances, or the passivation of the catalyst, enable uncomplicated and safe handling and storage of the catalyst. The catalyst may then have to be freed of the inert liquid before the start of the actual reaction, or the passivation layer has to be removed, for example by treating with hydrogen or a hydrogen-comprising gas.

Before the start of the hydroamination, the catalyst can be freed from the inert liquid or passivation layer. This is done, for example, by the treatment with hydrogen or a hydrogen-comprising gas. The hydroamination is preferably undertaken directly after the reduction of the catalyst precursor in the same reactor in which the reduction was also effected.

Catalyst precursors can, however, also be used in the process without prereduction, in which case they are reduced under the conditions of the hydrogenating amination by the hydrogen present in the reactor, the catalyst generally being formed in situ. Before it is used in stage b), the hydrogenation catalyst can be freed from the inert liquid or passivation layer. This is done, for example, by the treatment of the hydrogenation catalyst with hydrogen or a hydrogen-comprising gas. Preference is given to undertaking stage b) directly after the treatment of the hydrogenation catalyst in the same reactor in which the hydrogenation catalyst was also treated with hydrogen or a hydrogen-comprising gas.

Catalyst precursors can, however, also be used in the process without prereduction, in which case they are reduced by the hydrogen present in the reactor under the conditions of the hydrogenation which takes place in stage b), the hydrogenation catalyst generally being formed in situ.

The performance of stage b) (hydrogenation stage) can be performed batchwise or preferably continuously.

The performance of stage b) can be performed in the liquid phase or in the gas phase. Preference is given to performing stage b) in the liquid phase.

The reaction mixture obtained in stage a) can be reacted with hydrogen and ammonia in the presence of a solvent, preference being given to using the solvent which has already been used beforehand in stage a), for example in ethers such as methyl tert-butyl ether, ethyl tert-butyl ether or tetrahydrofuran (THF); alcohols such as methanol, ethanol or isopropanol; hydrocarbons such as hexane, heptane or raffinate cuts; aromatics such as toluene; amides such as dimethylformamide or dimethylacetamide, or lactams such as N-methylpyrrolidone, N-ethylpyrrolidone, N-methylcaprolactam or N-ethylcaprolactam. Useful solvents also include suitable mixtures of the solvents listed above. The solvent can be used in a proportion of 5 to 95% by weight, preferably 20 to 70%, more preferably 30 to 60%, based in each case on the total weight of the reaction mixture from stage a) and solvent.

Preference is given to performing the reaction of acrolein with secondary amine without an addition of solvent.

The batchwise performance of the hydrogenation stage (stage b)) can be performed, for example, in a stirred autoclave, a bubble column or a circulation reactor, for instance a jet loop reactor.

In the batchwise performance of the hydrogenation stage, a suspension of the reaction mixture from stage a) and hydrogenation catalyst and optionally solvent is typically initially charged in the reactor. In order to ensure a high conversion and high selectivity, the suspension of the reaction mixture from stage a) and catalyst with ammonia is typically mixed thoroughly, for example by means of a turbine stirrer in an autoclave.

The suspended catalyst material can be introduced and removed again with the aid of customary techniques (sedimentation, centrifugation, cake filtration, crossflow filtration). The catalyst can be used once or more than once.

The catalyst concentration is advantageously 0.1 to 50% by weight, preferably 0.5 to 40% by weight, more preferably 1 to 30% by weight, especially 5 to 20% by weight, based in each case on the total weight of the suspension consisting of the reaction mixture from stage a) and catalyst.

The mean catalyst particle size is advantageously in the range from 0.001 to 1 mm, preferably in the range from 0.005 to 0.5 mm, especially from 0.01 to 0.25 mm. In the case of batchwise performance of stage b), the pressure is generally 1-400 bar, preferably 5 to 300 bar, more preferably 10 to 250 bar, especially preferably 30 to 100 bar.

According to the invention, the temperature is (−50) to 70° C., preferably 0 to 70° C., more preferably 20 to 70° C. and especially 35 to 65° C. In a further embodiment, the temperature is (−50) to 39° C., preferably 0 to 39° C. and more preferably 10 to 39° C.

The hydrogenation stage is preferably performed continuously, typically in pressure vessels or pressure vessel cascades.

In the case of continuous performance of stage b) in the liquid phase, the reaction mixture from stage a) including hydrogen and ammonia is preferably passed over the hydrogenation catalyst, which is preferably present in a fixed bed reactor. Both trickle mode and liquid phase mode are possible.

In the case of continuous performance of stage b) in the liquid phase, the pressure is generally 1-400 bar, preferably 5 to 300 bar, more preferably 10 to 250 bar, especially preferably 30 to 100 bar.

According to the invention, the temperature is (−50) to 70° C., preferably 0 to 70° C., more preferably 20 to 70° C. and especially 35 to 65° C. In a further embodiment, the temperature is (−50) to 39° C., preferably 0 to 39° C. and more preferably 10 to 39° C. In the case of continuous performance of stage b) in the gas phase, the reaction mixture from stage a) is passed over the catalyst together with ammonia in a gas stream selected on a sufficiently large scale for evaporation, in the presence of hydrogen.

In the case of performance of stage b) in the gas phase, the pressure is generally 0.1-400 bar, preferably 1 to 100 bar, more preferably 1 to 50 bar. According to the invention, the temperature is (−50) to 70° C., preferably 0 to 70° C., more preferably 20 to 70° C. and especially 35 to 65° C. In a further embodiment, the temperature is (−50) to 39° C., preferably 0 to 39° C. and more preferably 10 to 39° C.

The catalyst hourly space velocity in the case of continuous performance of stage b) is generally in the range from 0.05 to 20 kg, preferably 0.1 to 15 kg and more preferably 0.2 to 10 kg of reaction mixture from stage a) per liter of catalyst (bed volume) and hour.

The reaction mixture obtained in stage b) comprises N,N-substituted 3-propan-1-ols.

Before further use or further processing, the reaction mixture obtained in stage b) can be worked up in order to concentrate the N,N-substituted 3-aminopropan-1-ol, for example by distillation or rectification.

Unconverted reactants, such as secondary amines, hydrogen or ammonia, can be recycled into the process.

DMAPOL can be used as a catalyst for polyurethane preparation and as a scrubbing fluid in gas scrubbing. In addition, DMAPOL can be used in the electronics chemicals and electroplating sectors.

In addition, DMAPOL is an important feedstock in organic synthesis and can be used, for example, as an intermediate in the production of pharmaceuticals and crop protection compositions.

The present invention accordingly also relates to the use of the DMAPOL obtainable in accordance with the invention in the aforementioned fields of use.

One advantage of the invention lies in the provision of a process for preparing N,N-substituted 3-aminopropan-1-ols from acrolein, in which a high selectivity based on the acrolein used is achieved. By virtue of the fact that the N,N,N',N'-substituted 1,3-propenediamines obtained as an intermediate need not be isolated or purified before the further conversion to N,N-substituted 3-aminopropan-1-ol, the process is easy to manage and industrially implementable. The present invention provides a new preparation route for DMAPOL, in which feedstocks which can be obtained on the basis of renewable raw materials are used. In addition, the target products (N,N-substituted 3-aminopropan-1-ols) are formed with high selectivity. A further advantage of the process according to the invention is that, in stage b), it is possible to use a hydrogenation catalyst which is less expensive compared to the prior art Pt catalysts used.

The invention is illustrated in detail by the examples which follow.

EXAMPLE 1

A 270 ml autoclave was initially charged with 33.8 g of dimethylamine (0.75 mol) and 30 g of THF, and 16.8 g of acrolein (0.3 mol) in 30 g of THF were pumped in with cooling (4° C.) over 60 minutes. The mixture was stirred for 15 minutes. A sample was taken and analyzed by means of gas chromatography. The contents of this autoclave were then transferred by means of a connecting line by injection of hydrogen into a 270 ml high-pressure autoclave which had already been charged with 1.8 g of Ra—Co (THF-washed) in 25.5 g of NH3 (1.5 mol). The second autoclave was heated to 40° C. and hydrogen was injected to 60 bar. Hydrogenation was then effected for 3 hours and the pressure was maintained by adding hydrogen. After 3 hours, a sample was taken and analyzed by means of gas chromatography. By gas chromatography analysis of a sample, it was found that 91.5 GC area % of the desired N,N-dimethyl-3-aminopropan-1-ol (DMAPOL) product had formed. In addition, 4.6 GC area % of N,N-dimethylpropanediamine (DMAPA) was found.

EXAMPLE 2

A 270 ml autoclave was initially charged with 67.6 g of dimethylamine (1.5 mol) and 16.8 g of acrolein (0.3 mol) were pumped in with cooling (4° C.) over 60 minutes. The mixture was stirred for 15 minutes. A sample was taken and analyzed by means of gas chromatography. The contents of this autoclave were then transferred by means of a connecting line by injection of hydrogen into a 270 ml high-pressure autoclave which had already been charged with 1.8 g of Ra—Co (THF-washed) in 51.0 g of NH3 (3 mol). The second autoclave was heated to 40° C. and hydrogen was injected to 60 bar. Hydrogenation was then effected for 4 hours and the pressure was maintained by adding hydrogen. After 4 hours, a sample was taken and analyzed by means of gas chromatography. By gas chromatography analysis of a sample, it was found that 91.4 GC area % of the desired N,N-dimethyl-3-aminopropan-1-ol (DMAPOL) product had formed. In addition, 4.5 GC area % of N,N-dimethyl-propanediamine (DMAPA) was found.

EXAMPLE 3

A 270 ml autoclave was initially charged with 67.6 g of dimethylamine (1.5 mol) and 16.8 g of acrolein (0.3 mol) were pumped in with cooling (4° C.) over 60 minutes. The mixture was stirred for 15 minutes. A sample was taken and analyzed by means of gas chromatography. The contents of this autoclave were then transferred by means of a connecting line by injection of hydrogen into a 270 ml high-pressure autoclave which had already been charged with 1.8 g of Ra—Co (THF-washed) in 51.0 g of NH3 (3 mol) and 10.8 g of water (0.6 mol). The second autoclave was heated to 23° C. and hydrogen was injected to 60 bar. Hydrogenation was then effected for 6 hours and the pressure was maintained by adding hydrogen. After 6 hours, a sample was taken and analyzed by means of gas chromatography. By gas chromatography analysis of a sample, it was found that 58.3 GC area % of the desired N,N-dimethyl-3-aminopropan-1-ol (DMAPOL) product had formed. In addition, 4.0 GC area % of N,N-dimethyl-propanediamine (DMAPA) was found.

EXAMPLE 4

A 270 ml autoclave was initially charged with 67.6 g of dimethylamine (1.5 mol) and 16.8 g of acrolein (0.3 mol) were pumped in with cooling (4° C.) over 60 minutes. The mixture was stirred for 15 minutes. A sample was taken and analyzed by means of gas chromatography. The contents of this autoclave were then transferred by means of a connecting line by injection of hydrogen into a 270 ml high-pressure autoclave which had already been charged with 1.8 g of Ra—Co (THF-washed) in 51.0 g of NH3 (3 mol) and 10.8 g of water (0.6 mol). The second autoclave was heated to 60° C. and hydrogen was injected to 60 bar. Hydrogenation was then effected for 2 hours and the pressure was maintained by adding hydrogen. After 2 hours, a sample was taken and analyzed by means of gas chromatography. By gas chromatography analysis of a sample, it was found that 33.8 GC area % of the desired N,N-dimethyl-3-aminopropan-1-ol (DMAPOL) product had formed. In addition, 58.2 GC area % of N,N-dimethylpropanediamine (DMAPA) was found.

EXAMPLE 5

A 270 ml autoclave was initially charged with 67.6 g of dimethylamine (1.5 mol) and 16.8 g of acrolein (0.3 mol) were pumped in with cooling (4° C.) over 60 minutes. The mixture was stirred for 15 minutes. A sample was taken and analyzed by means of gas chromatography. The contents of this autoclave were then transferred by means of a connecting line by injection of hydrogen into a 270 ml high-pressure autoclave which had already been charged with 1.8 g of Ra—Co (THF-washed) in 51.0 g of NH3 (3 mol) and 10.8 g of water (0.6 mol). The second autoclave was heated to 40° C. and hydrogen was injected to 60 bar. Hydrogenation was then effected for 3 hours and the pressure was maintained by adding hydrogen. After 3 hours, a sample was taken and analyzed by means of gas chromatography. By gas chromatography analysis of a sample, it was found that 57.5 GC area % of the desired N,N-dimethyl-3-aminopropan-1-ol (DMAPOL) product had formed. In addition, 29.4 GC area % of N,N-dimethylpropanediamine (DMAPA) was found.

COMPARATIVE EXAMPLE 1

The procedure was analogous to example 5, except that stage b) was performed at a temperature of 100° C. By gas chromatography analysis of a sample, it was found that 0.4 GC area % of the desired N,N-dimethyl-3-aminopropan-1-ol (DMAPOL) product had formed. In addition, 91.4 GC area % of N,N-dimethylpropanediamine (DMAPA) was found.

COMPARATIVE EXAMPLE 2

The procedure was analogous to example 5, except that stage b) was performed at a temperature of 80° C. By gas chromatography analysis of a sample, it was found that 13.9 GC area % of the desired N,N-dimethyl-3-aminopropan-1-ol (DMAPOL) product had formed. In addition, 80.3 GC area % of N,N-dimethylpropanediamine (DMAPA) was found.

The invention claimed is:

1. A process for preparing N,N-substituted 3-aminopropan-1-ols by
   a) reacting secondary amine with acrolein at a temperature of (−50) to 100° C. and a pressure of 0.01 to 300 bar, and
   b) reacting the reaction mixture obtained in stage a) with hydrogen and ammonia in the presence of a hydrogenation catalyst at a pressure of 1 to 400 bar,
   wherein the molar ratio of secondary amine to acrolein in stage a) is 1:1 or more, the temperature in stage b) is in the range from 20 to 70° C., and stage b) is performed in the presence of water.

2. The process according to claim 1, wherein the molar ratio of secondary amine to acrolein is 2:1 to 50:1.

3. The process according to claim 1, wherein stage b) is performed at a pressure of 20 to 250 bar.

4. The process according to claim 1, wherein the molar ratio of the ammonia used in stage b) to the acrolein used in stage a) is 2:1 to 100:1.

5. The process according to claim 1, wherein the hydrogenation catalyst is present in metallic form.

6. The process according to claim 4, wherein the molar proportion of cobalt atoms based on the sum of all metal atoms in the hydrogenation catalyst used, which is used in the process in metallic form, is 50 mol % and more.

7. The process according to claim 5, wherein the hydrogenation catalyst in metallic form is a Raney sponge or skeletal catalyst.

8. The process according to claim 1, wherein the hydrogenation catalyst is obtained by reducing the catalyst precursors which comprise one or more catalytically active components in the form of oxygen compounds of groups 8 and/or 9 and/or 10 and/or 11 of the Periodic Table of the Elements.

9. The process according to claim 8, wherein the molar proportion of cobalt atoms based on the sum of all metal atoms present in the catalytically active components used is 30 mol % or more.

10. The process according to claim 1, wherein the reaction mixture obtained in stage a), before use in stage b), is used without additional purification or workup.

11. The process according to claim 1, wherein the secondary amine is selected from the group consisting of dimethylamine, diethylamine, di-n-propylamine, diisopropylamine, isopropylethylamine, di-n-butylamine, di-s-butylamine and dicyclohexylamine.

12. The process according to claim 11, wherein the secondary amine is dimethylamine.

13. The process according to claim 1, wherein the molar ratio of water to acrolein used is in the range from 0.01:1 to 2:1.

14. The process according to claim 1, wherein acrolein which has been prepared from glycerol is used.

15. The process according to claim 14, wherein the glycerol is glycerol obtained as a by-product from fat hydrolysis or biodiesel production.

* * * * *

UNITED STATES PATENT AND TRADEMARK OFFICE
CERTIFICATE OF CORRECTION

PATENT NO.       : 8,536,377 B2                                             Page 1 of 1
APPLICATION NO. : 13/127828
DATED            : September 17, 2013
INVENTOR(S)      : Wigbers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 223 days.

Signed and Sealed this

Fifteenth Day of September, 2015

Michelle K. Lee
*Director of the United States Patent and Trademark Office*